United States Patent
Dombeck

(10) Patent No.: US 7,154,282 B1
(45) Date of Patent: Dec. 26, 2006

(54) SYSTEM AND METHOD FOR CALIBRATING MOISTURE METERS WITH ASSOCIATED SETTABLE SLURRY PRODUCTS FOR DETERMINING RELATIVE DRYNESS

(75) Inventor: Russell A. Dombeck, Salem, WI (US)

(73) Assignee: United States Gypsum Company, Chicago, IL (US)

( * ) Notice: Subject to any disclaimer, the term of this patent is extended or adjusted under 35 U.S.C. 154(b) by 0 days.

(21) Appl. No.: 11/230,152

(22) Filed: Sep. 19, 2005

(51) Int. Cl.
*G01R 35/00* (2006.01)

(52) U.S. Cl. ...................................... 324/601; 324/694

(58) Field of Classification Search .............. 324/601, 324/694
See application file for complete search history.

(56) References Cited

U.S. PATENT DOCUMENTS 5,313,167 A * 5/1994 Marshall ..................... 324/632
6,104,200 A * 8/2000 Hook ........................ 324/643
6,204,670 B1 * 3/2001 Joshi ......................... 324/643

OTHER PUBLICATIONS

Moisture Register Products, "RF Sensors for the BSP-901 and Smart Systems", http://www.moistureregisterproducts.com/RFSENS.HTM, Aug. 25, 2005.

* cited by examiner

*Primary Examiner*—Vincent Q. Nguyen
(74) *Attorney, Agent, or Firm*—Greer, Burns & Crain, Ltd.; Michael M. Geoffrey; David F. Janci

(57) ABSTRACT

A method is provided for calibrating a moisture meter to a particular settable slurry product for determining the relative dryness of the product. The steps of the method include determining the appropriate relative dryness of the particular slurry product, associating a moisture meter reading with the appropriate relative dryness to achieve a meter value, determining the relative spacing of the meter from a conductive surface for obtaining the associated meter value and providing a spacer having the relative spacing for calibrating subsequent meters for measuring the relative dryness of the settable slurry product.

4 Claims, 3 Drawing Sheets

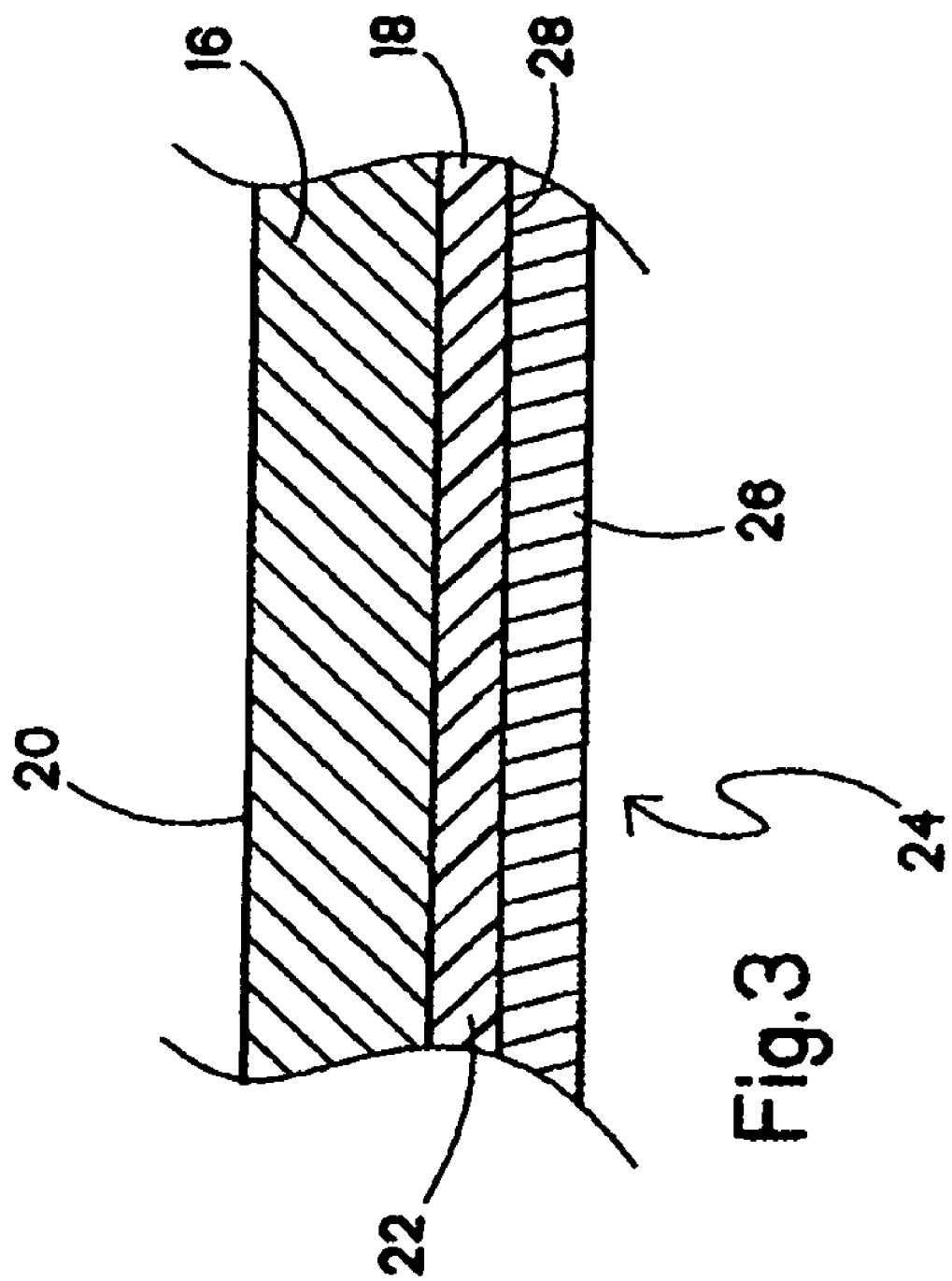

SYSTEM AND METHOD FOR CALIBRATING MOISTURE METERS WITH ASSOCIATED SETTABLE SLURRY PRODUCTS FOR DETERMINING RELATIVE DRYNESS

BACKGROUND OF THE INVENTION

The present invention relates generally to the use of settable slurries in the construction industry for providing level underlayments for floors, walls etc., and more specifically provides a system for reliably determining the degree of dryness of such slurries prior to the application of a final surfacing material such as, but not limited to tile, sheet vinyl, wood, carpet, wall covering or the like.

In the construction industry, whether in new construction or remodeled spaces, before a final surface coating or covering is applied, including but not limited to tile, sheet flooring, wood flooring, carpeting, a leveling product is typically applied to level the base floor in preparation for the final coating. One such product is sold under the brand LEVELROCK® by United States Gypsum Company, the owner of the present invention. LEVELROCK® compound is a gypsum based product which is mixed with water and sand to form a pourable slurry that is applied to floors for leveling purposes. It is important to users of LEVELROCK® compound or similar products that the product is sufficiently dry prior to applying the final surfacing material. If the product is not dry enough, the moisture has been known to attack the bonding agent of certain adhesives, causing the final surfacing material to fail to properly adhere to the leveling product or the substrate. In some cases, buckling or blistering of the final surfacing material may result. Since the drying process of such leveling compounds may take several days, it is important for construction budgeting and workload considerations that the appropriate moisture level be accurately determined as soon as possible.

One attempted solution of this problem is to employ moisture meters to determine the relative dryness of the leveling product. Such meters are typically used in construction, home inspections or similar activities for measuring the moisture level of wood or concrete. Such meters have proved unsatisfactory in reliably measuring the relative dryness of leveling products, since the values displayed often do not accurately reflect the dryness of leveling compounds in general, and also for the specific product, because the meters are not commonly designed for such readings. In addition, meters vary in sensitivity among manufacturers, and also between units of the same manufacturer and model.

In the wallboard manufacturing process, relatively sensitive moisture meters have been employed for determining the desired moisture characteristics of setting wallboard on a wallboard manufacturing conveyor line. Prior to installing the meters upon a conveyor line, it is known to use spacers representing the desired wallboard thickness in calibrating the meter. Exemplary spacer thicknesses are 0.25 inch, 0.5 inch, 0.75 inch, representing standard wallboard thicknesses. The spacers are manufactured of phenolic plastic, which has a dielectric, or inherent radiation deflecting properties which simulate moderately wet wallboard. Calibration is performed by generating two values, a first based on the dielectric of air, creating a "zero" value, and another value using the spacers, approximating the moderately wet wallboard. In such applications, once calibrated, the meter monitors moisture content from a specified distance from the wallboard surface. In some applications, the spacers have been replaced by merely moving the meter farther from the surface of the wallboard.

Such an arrangement has proved unsuitable for use in monitoring the moisture content or relative dryness of setting leveling compounds. One disadvantage of the above-described system is the fixed mounts for the meters to obtain a specified distance from the substrate, which is unsuitable for floor applications. Also, the nature of the meters used for wallboard monitoring is overly costly and cumbersome for use by flooring contractors. Furthermore, while wallboard moisture characteristics are fairly consistent, flooring contractors typically employ a variety of products depending on the application. There is a great variety in the drying characteristics among these various products, which defies consistent monitoring by the existing systems.

Thus, there is a need for an improved system for more accurately determining the relative dryness of leveling product prior to application of a final surfacing material. There is also a need for such an improved system which is usable with moisture meters from a variety of manufacturers. In addition, there is a need for an improved system of moisture monitoring which accommodates the variation in commercial products.

BRIEF SUMMARY OF THE INVENTION

The above-listed needs are met or exceeded by the present system for determining the moisture content, or level of relative dryness of settable slurry products such as leveling compounds and calibrating a meter for use with such a product. Featured in the present system is at least one spacer including a low conductive material which, through empirical testing, has a thickness associated with the appropriate relative dryness of a particular leveling compound or product. The spacer is associated with a relatively highly conductive metal plate on a surface opposite the meter. Prior to applying the meter to the leveling compound, the user places the meter upon the spacer, with the metal plate preferably situated on a substrate. The resulting reading will reflect the appropriate meter value displayed by the meter for the particular product when it is sufficiently dry. After noting the reading displayed by the meter upon the spacer, the user then places the meter on the leveling compound to be monitored. When the meter displays the same meter value as displayed upon the spacer, the user knows that the leveling compound is satisfactorily dry.

More specifically, a method is provided for calibrating a moisture meter to a particular settable slurry product for determining the relative dryness of the product. The steps of the method include determining the appropriate relative dryness of the particular slurry product, associating a moisture meter reading with the appropriate relative dryness to achieve a meter value, determining the relative spacing of the meter from a conductive surface for obtaining the associated meter value and providing a spacer having the relative spacing for calibrating subsequent meters for measuring the relative dryness of the settable slurry product.

In another embodiment, a method for determining the relative moisture of a particular settable slurry product includes providing a moisture meter, providing a spacer associated with the particular settable slurry product, placing the meter on the spacer to obtain a meter value, and removing the meter from the spacer and placing the meter upon the slurry to determine the relative dryness of the slurry product. A satisfactory reading is obtained once the meter displays the meter value when disposed upon the slurry product.

In still another embodiment, a system for determining the relative dryness of settable slurry products includes a moisture meter and a plurality of spacers each associated with a particular slurry product. Upon placement of the meter upon one of the spacers, the meter displays a meter value corresponding to the appropriate relative dryness of the particular slurry product, and upon removal of the meter from the spacer and placement of the meter upon the slurry product, the slurry product will have reached the appropriate relative dryness upon the meter displaying the meter value.

In yet another embodiment, a spacer is provided for use in a system for determining the relative dryness of a particular settable slurry product, the system including at least one spacer and a moisture meter. Upon placement of the meter upon a designated spacer, the meter displays a meter value corresponding to the appropriate relative dryness of the associated slurry product, and upon removal of the meter from said spacer and placement of the meter upon the slurry, the slurry will have reached the appropriate relative dryness upon the meter displaying the meter value. The spacer has a spacer element including a low conductivity material and a conductive element being joined to the spacer element and being conductive of radio waves generated by the meter.

In a still further embodiment, a kit for determining the relative dryness of settable slurry products using a moisture meter includes a plurality of spacers, each having at least one spacer element and a conductive element, each spacer element having a thickness associated with the desired relative dryness of a particular settable slurry product. Upon placement of the meter upon one of the spacers, the meter displays a meter value corresponding to the appropriate relative dryness of the associated slurry product, and upon removal of the meter from the spacer and placement of the meter upon the slurry, the slurry will have reached the appropriate relative dryness upon the meter displaying the meter value.

BRIEF DESCRIPTION OF THE SEVERAL VIEWS OF THE DRAWINGS

FIG. 3 is a fragmentary vertical section of an alternate embodiment to the spacer depicted in FIG. 1.

DETAILED DESCRIPTION OF THE INVENTION

The present method and system is intended for use with a variety of leveling products. In the preferred embodiment, the target products are applied over a surface such as a base or rough floor, or even horizontally disposed walls or wall segments as settable slurries, which can take as long as two to four days or even longer to reach the appropriate moisture level or relative dryness. Once the leveling product has reached the appropriate moisture level, the final surfacing material, such as tile, sheet vinyl carpet, wall covering or the like may be applied. It is important for effective adhesion of the final surfacing material to the base, that the leveling product is sufficiently dry.

To calibrate a meter for measuring a particular settable floor leveling product for determining the relative dryness of the product, it is first determined what level of moisture is desired in the final product to be sufficiently dry. This desired moisture level is the level at which final surfacing material will properly adhere. Such values, which may range from about 0.0 to 2.0% moisture (by weight of the final dry product), will vary with the leveling product and the desired final surfacing material. In many cases, a preferred moisture level is 1% or less.

Figure 1:
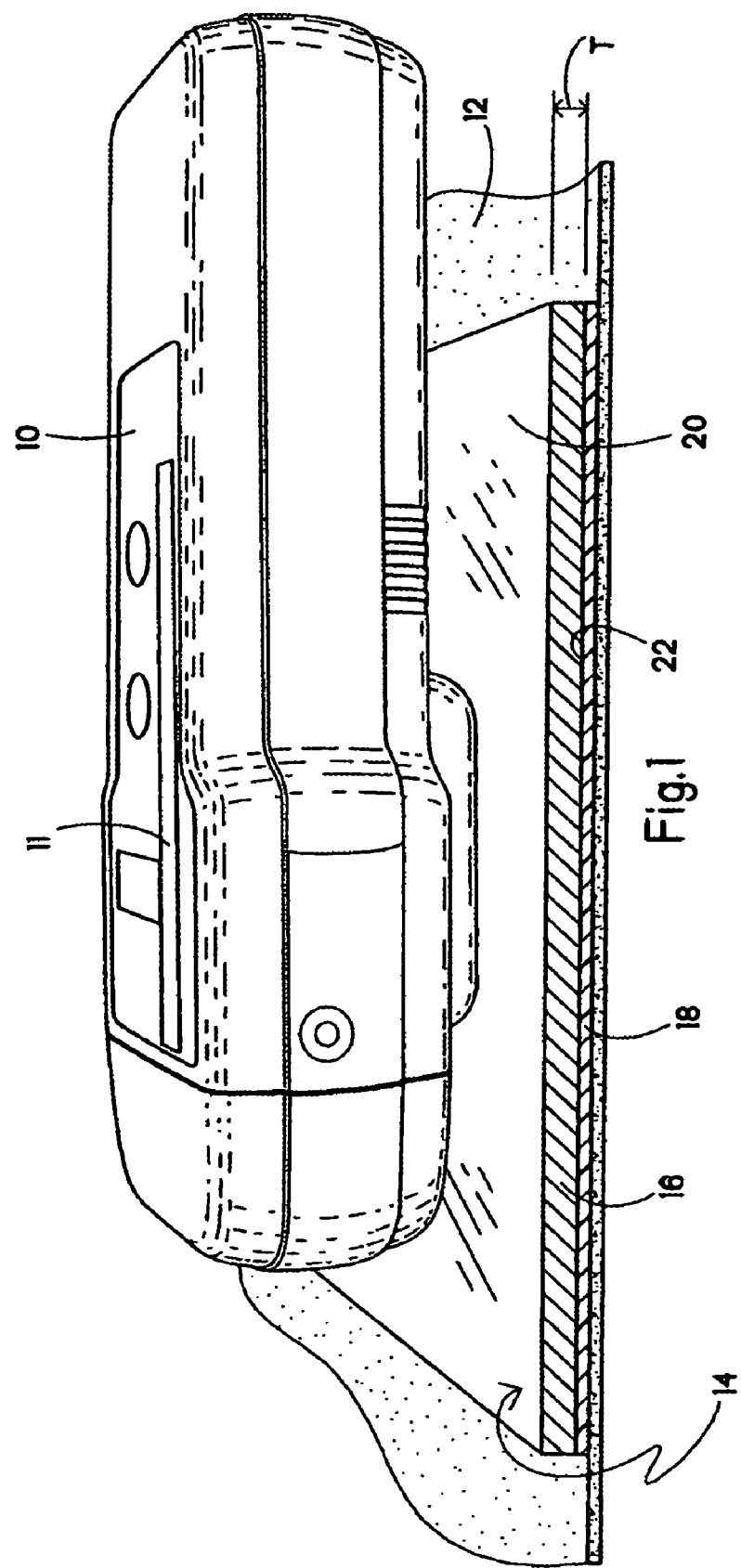
FIG. 1 is a top perspective view, in partial section, of a meter on a spacer according to the present system.

Referring now to FIG. 1, once the desired moisture level is determined for a particular floor leveling product, a designated meter 10 is used to associate a moisture meter reading with the appropriate relative dryness to achieve a meter value. This designated meter 10 will be used to set the standard for other meters used in the present system. The preferred meter 10 is of the radio frequency (RF) type, and a suitable example is the GE Protimeter Surveymaster manufactured by General Electric Co. It will be understood that there are a variety of competitive meters which are suitable for this task. Many suitable meters have distinct and irreconcilable display values. For example, the preferred Protimeter Surveymaster has a display 11 in which a sequence of colored LED's indicates the moisture level of the measured substrate.

For example, it has been determined that for a particular floor leveling compound, USG Levelrock 2500, the appropriate meter reading for the designated Protimeter Surveymaster meter at 1% moisture is 7 lighted or activated LED's. It will be understood that for any particular product, the meter reading may change when monitoring a desired moisture value, such as 1%. Such correlations between meter readings and moisture content are preferably tested empirically to properly utilize the present system. For example, several samples of the target leveling compound will be prepared, and when they reach the designated moisture level, i.e., 1%, a designated meter reading will be obtained to determine the appropriate value, referred to herein as the "meter value". Thus, for the above-identified Protimeter Surveymaster meter 10, the meter value for USG Levelrock 2500 product at 1% moisture is 7 lighted or activated LED's.

Figure 2:
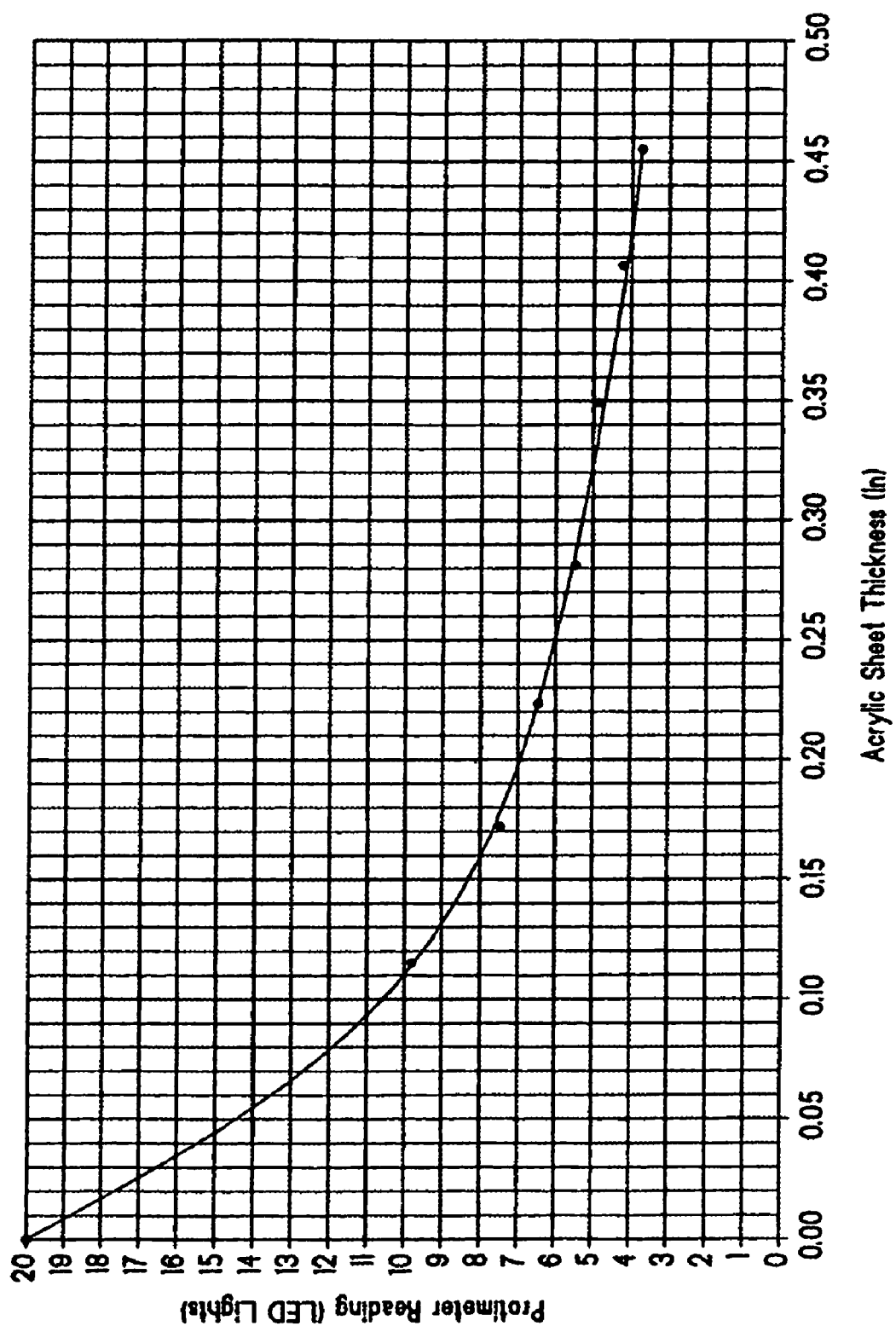
FIG. 2 is a graph of meter readings for a particular settable slurry product as a function of spacer thickness.

Next, the designated meter 10 is moved to a substrate 12 such as a non-conductive table or workbench to determine the desired meter spacing, or the thickness of a desired spacer which will be used to reproduce the meter value when other meters are used to measure moisture on the same leveling product. Referring to FIG. 2, it is known that the farther a meter of this type is displaced from a test surface, the displayed reading will decrease. It has been found that once a consistent spacing is determined, the meter value will be repeatable, as long as the meter is of the same RF type, regardless of the manufacturer or the particular display scale. Referring again to FIG. 1, to obtain desired results, the properties and construction of a spacer, generally designated 14 which cause the meter 10 to display the meter value should meet the following parameters. First, the spacer 14 is preferably made of two main components: at least one low conductivity spacer element 16 and a relatively highly conductive element 18. The spacer element 16 is contemplated as being made of a number of materials, including plastic or glass which has consistent RF transmission qualities. By "low conductivity", it is meant that under normal environmental conditions, and relative to the voltage emitted by the meter 10, the spacer element 16 will be an insulator with consistent transmission properties. It is appreciated that suitable insulators can still have some conductivity and be suitable as the spacer element 16, provided the resulting reading is within the displayed range of the meter 10. An important property employed in dimensioning the spacer element 16 is that the farther the meter 10 is placed from the conductive element 18, the lower the displayed reading. A preferred plastic is acrylic or high density polyethylene, and phenolic plastics such as Bakelite have proven unsuitable for the present spacers because of variability in their dielectric properties. Preferred spacer element materials have a dielectric constant of less than 10. Also, while solid planar sheets of spacer element 16 are preferred, it is also contemplated that hollow tubes or other nonsolid or irregularly shaped spacers could be provided to define a layer of air between the meter 10 and the conductive element 18, as long as they have a specified, constant thickness 'T' or height. It is contemplated that the thickness 'T' will vary with spacer material.

Further, the conductive element 18 is preferably a metal sheet which is generally conductive of the radiation emitted by the meter 10. Thus, steel, aluminum, copper, brass and alloys of same and equivalent metals are considered acceptable. It is important that the conductive element 18 have a surface area large enough to encompass most of the electric field generated by the meter 10. The preferred size for the conductive sheet is in the range of 6 inches (15 cm) of diameter on a circular element, or per side in a square or rectangular conductive element. Other sizes are contemplated depending on the power of the particular meter 10.

It is also preferred that the spacer element 16 is secured to the conductive element 18, as by chemical adhesive, ultrasonic welding, fusion or similar technologies. One suitable adhesive is a spray adhesive product manufactured by 3M Corporation. By securing the spacer element 16 to the conductive element 18 the respective desired spacing between the meter 10 and the conductive element is maintained. Thus, by either placing spacers or shims between the meter 10 and the conductive element 18, or by physically moving the meter relative to the conductive element, the meter is placed a suitable distance from the conductive element so that the meter displays the meter value. Accordingly, a first surface 20 of the spacer element 16 accommodates the moisture meter 10, and a reverse surface 22 engages and is joined to the conductive element 18.

Once the appropriate spacing 'T' is determined for the designated meter 10 for a particular leveling product, the same spacing is usable for other RF meters of the same or other manufacturers as the designated meter. In the present example, the spacing 'T' for the designated meter 10 for the Levelrock 2500 product is 0.20 inch. It is contemplated that a range of variation in the spacer thickness of ± about 0.03 inch is acceptable, with a tolerance of 0.01 inch preferable. It is also contemplated that, depending on the type of leveling product, the spacing 'T' will range between about 0.10 and 0.5 inch.

In practice, a supplier of leveling products preferably provides a set or kit of spacers 14, each dimensioned with a spacing corresponding to a particular product in the supplier's line, and at the designated moisture level. In some cases, it is contemplated that the supplier can provide a meter with the spacers 14. Using an RF-style meter to determine whether a particular leveling product is sufficiently dry, the user places the meter on the corresponding spacer 14 to obtain a meter value. Next, the user removes the meter from the spacer 14 and places the meter upon the setting slurry to determine the relative dryness of the slurry product. If the meter reading is higher than the meter value, the product is not sufficiently dry. Once the meter located on the leveling product displays the meter value, the product is sufficiently dry, and appropriate final surface coating can be safely applied.

Referring now to FIG. 3, an alternate embodiment of the spacer 14 is generally designated 24. Components shared with the spacer 14 are designated with the same reference numbers. A main difference between the spacer 24 and the spacer 14 is that the spacer 24 has a second spacer element 26 secured to a reverse surface 28 of the conductive element 18 from the spacer element 16. It is contemplated that the second spacer element 26 is secured to the conductive element 18 in the same manner as the spacer element 16. Thus, for one leveling product, the user employs the spacer element 16, and for another leveling product with distinct drying properties, the user employs the spacer element 26 for obtaining a distinct meter value associated with the different leveling product.

While particular embodiments of the present system and method for calibrating moisture meters with associated settable slurry products for determining relative dryness have been described herein, it will be appreciated by those skilled in the art that changes and modifications may be made thereto without departing from the invention in its broader aspects and as set forth in the following claims.

The invention claimed is:

1. A method for calibrating a moisture meter to a particular settable slurry product for determining the relative dryness of the product, comprising:
   determining the appropriate relative dryness of the particular slurry product;
   associating a moisture meter reading with the appropriate relative dryness to achieve a meter value;
   determining the relative spacing of the meter from a conductive surface for obtaining the associated meter value; and
   providing a spacer having the relative spacing from said conductive surface for calibrating subsequent meters for measuring the relative dryness of the settable slurry product.

2. The method of claim 1 wherein the spacer includes at least one low conductivity spacer element associated with a conductive element used as a unit, such that the spacer is disposed between the meter and the conductive element.

3. The method of claim 2 wherein said at least one spacer element includes a first spacer element on one surface of said conductive element, and a second spacer element on a reverse surface of said conductive element.

4. The method of claim 2 wherein said conductive element is conductive of radio frequencies generated by the meter.

* * * * *